United States Patent [19]

Johs et al.

[11] Patent Number: 5,666,201
[45] Date of Patent: *Sep. 9, 1997

[54] MULTIPLE ORDER DISPERSIVE OPTICS SYSTEM AND METHOD OF USE

[75] Inventors: Blaine D. Johs; Ping He; Steven E. Green; Shakil A. Pittal; John A. Woollam, all of Lincoln, Nebr.

[73] Assignee: J.A. Woollam Co. Inc., Lincoln, Nebr.

[*] Notice: The term of this patent shall not extend beyond the expiration date of Pat. No. 5,373,359.

[21] Appl. No.: 530,892

[22] Filed: Sep. 20, 1995

Related U.S. Application Data

[63] Continuation-in-part of Ser. No. 265,325, Jun. 24, 1994, Pat. No. 5,521,706, and a continuation of Ser. No. 339,834, Nov. 14, 1994, Pat. No. 5,504,582, which is a continuation-in-part of Ser. No. 947,430, Sep. 18, 1992, Pat. No. 5,373,359.

[51] Int. Cl.[6] .................................................. G01N 21/21
[52] U.S. Cl. .................................. 356/369; 250/225
[58] Field of Search .......................... 356/369, 364–368; 250/225

[56] References Cited

U.S. PATENT DOCUMENTS

| 4,030,835 | 6/1977 | Firester et al. . | |
|---|---|---|---|
| 4,158,506 | 6/1979 | Collett . | |
| 4,200,396 | 4/1980 | Kleinknecht et al. . | |
| 4,236,823 | 12/1980 | Roach et al. . | |
| 4,541,716 | 9/1985 | Crooks et al. . | |
| 4,681,450 | 7/1987 | Azzam . | |
| 4,725,145 | 2/1988 | Azzam . | |
| 5,081,348 | 1/1992 | Siddiqui . | |
| 5,102,222 | 4/1992 | Berger et al. . | |
| 5,337,146 | 8/1994 | Azzam . | |
| 5,373,359 | 12/1994 | Woollam et al. | 356/369 |
| 5,504,582 | 4/1996 | Johs et al. | 356/369 |
| 5,521,706 | 5/1996 | Green et al. | 356/369 |

FOREIGN PATENT DOCUMENTS

2069691  2/1980  United Kingdom .

OTHER PUBLICATIONS

Division–of–Amplitude Photopolarimeter based on conical diffraction from a metallic grating, Applied Options, vol. 31, No 19, 1, Jan. 13, 1992, 277 and pp. 424–431 HECHT, "OPTICS", 2nd Ed. Addison–Wesley, 1987.

Primary Examiner—Hoa Q. Pham
Attorney, Agent, or Firm—James D. Welch

[57] ABSTRACT

Disclosed is a dispersive optics system, in the context of ellipsometer or polarimeter and the like systems, which, in use, produces a plurality of "Orders" of essentially single wavelength beams of light from a polychromatic beam of light. In use the availability of more than one "Order" of essentially single wavelength beams of light allows simultaneous measurement of more essentially single wavelength beams of light than would be possible were only one "Order" of essentially single wavelength beams of light present. Filters are present to reduce the effects of stray light on detector elements and to allow separating the wavelengths in overlapping regions of adjacent Orders.

20 Claims, 3 Drawing Sheets

MULTIPLE ORDER DISPERSIVE OPTICS SYSTEM AND METHOD OF USE

This Application is a Continuation-In-Part of application Ser. Nos. 08/265,325 (filed Jun. 24, 1994), and 08/339,834, (now U.S. Pat. Nos. 5,521,706 and 5,504,582 respectively), (filed Nov. 14, 1994), which in turn are Continuation-In-Part applications of patent application Ser. No. 07/947,430 (filed Sep. 18, 1992), now U.S. Pat. No. 5,373,359.

TECHNICAL FIELD

The present invention relates to ellipsometer or polarimeter and the like systems, and more particularly to spectroscopic ellipsometer or polarimeter and the like systems which enable simultaneous analysis of measured signals derived from a multiplicity of essentially single wavelength beams of light, which essentially single wavelength beams of light are produced by interaction with a multiple "Order" producing dispersive optics. The present invention system includes one or more filter(s), each comprised of one or more elements, to eliminate the effects of stray light on detector elements, and to separate wavelengths present in overlapping portions of adjacent Orders.

BACKGROUND

Ellipsometer or Polarimeter and the like systems, allow determination of Sample System physical and optical properties, (such as thickness, refractive index and extinction coefficient of surface films thereon, by detecting change in the "Polarization State" of a beam of polarized light which is caused to interact with said Sample System, where Polarization State here refers to a set of values for Polarized Light Beam Quadrature Components, (such as "S" and "P"), Magnitude Ratio, and a Phase Angle therebetween. (It is noted that "P" refers to that component which is in a plane containing the normal to a Sample System and incident and/or transmitted beam(s) of polarized light, and "S" refers to that component perpendicular thereto and parallel to the surface of said Sample System. It is also noted that a "full" polarization state also requires designation of an absolute value to which a magnitude ratio is referenced, and the direction of rotation of a polarized beam of light).

Ellipsometer Systems generally can be broadly classified as Rotatable or Intensity Modulating Rotating Element Ellipsometers (REE) and Phase Modulating Modulation Element Ellipsometers (MEE). For instance, a Patent to Woollam et al., U.S. Pat. No. 5,373,359, describes a Rotating Analyzer Ellipsometer (RAE) in which a Light Source provided beam of light is caused to pass through a Polarizer, (which serves to set a Polarization State therein), then interact with a Sample System. Said interaction with said Sample System serves to alter the Polarization State of said polarized beam of light, which polarized beam of light then sequentially encounters a Rotating Analyzer and a Dispersion Optics, (e.g. a Diffraction Grating is specified), which forms therefrom a multiplicity of essentially single wavelength polarized beams of light. Said multiplicity of essentially single wavelength polarized beams of light are then caused to enter a Photo Detector Array, in which Photo Detector Array, individual Detector Elements serve to develop a representative signal for each. Fourier Analysis, for instance, of said signals allows determination of parameters which allow determination of Sample System characterizing PSI and DELTA values. It is noted that in said Woollam et al. (RAE) there is no additional focusing applied after the polarized beam of light encounters the Sample System. Another Patent, to Ducharme et al. U.S. Pat. No. 5,416,588, on the other hand, describes a Modulation Element Ellipsometer (MEE) comprised of a Light Source, a Polarizer, a Polarization State Modulator Element, a means for splitting Quadrature Components in a Beam of Polarized Light after interaction with a Sample System, two Detector Elements and an Analysis System. In use a beam of light is provided by the Light Source and a state of Polarization is set therein by said Polarizer, after which the polarized beam of light is subjected to a Polarization State Modulation and caused to interact with a Sample System, which Sample System changes the State of Polarization of said Phase Modulated Polarized beam of light. Quadrature Components of said Polarized beam of Light are then isolated and subjected to separate, for instance, Fourier Analysis. Appropriate utilization of the Coefficients of the terms of a Fourier Series allows determination of Sample System characterizing PSI and DELTA values. It is noted the described Modulation Element Ellipsometer (MEE) utilizes Coefficients from Fourier Series based upon both Quadrature Components. Some Modulation Ellipsometers utilize Fourier Series Coefficients based upon only one such Quadrature Component. While the specifics of signal generation are different in (REE) and (MEE) ellipsometers, and even amongst Ellipsometers of similar type, the end result of utilization thereof is provision of PSI and DELTA values for Sample Systems analyzed therein. This is the case regardless of Sample System type (e.g. isotropic, anisotropic or anisotropic and depolarizing).

In the above the terms Polarizer and Analyzer were utilized, and it is to be understood that said elements can be essentially similar and are identified primarily by location in an Ellipsometer or Polarizer and the like system. Polarizers are positioned ahead of a Sample System, and Analyzers thereafter. As well, Compensators can be present, for instance, between Polarizers and Analyzers, and after Analyzers. Compensators generally operate to change a phase angle between quadrature components of a polarized beam of light, via a birefringence property which serves to retard one quadrature component differently than the other. Polarizers, Analyzers and Compensators can be Rotatable, Rotating and Stationary in use.

Numerous other Ellipsometer Systems could be described, which are, for instance, comprised of various combinations of:

Stationary Polarizer(s);
Stationary Compensator(s);
Stationary Analyzer(s);
Rotatable Polarizer(s);
Rotatable Compensator(s);
Rotatable Analyzer(s);
Rotating Polarizer(s);
Rotating Compensator(s);
Rotating Analyzer(s);
Modulator Element(s).

Examples of Ellipsometers to which the present invention system and method of application can be applied are, for instance:

a. Rotatable Element Nulling Ellipsometers (RENE);
b. Rotatable Element Automated Nulling Ellipsometers (REANE);
c. Modulation Element Ellipsometers (MEE);
d. Rotating Analyzer Ellipsometers (RAE);
e. Rotating Polarizer Ellipsometers (RPE);

f. Rotating Compensator Ellipsometers (RCE);

g. Rotating Polarizer and Analyzer Ellipsometers (RPAE);

h. Rotating Polarizer and Analyzer, Fixed Compensator (RPAFCE);

i. Rotating Analyzer and Compensator, Fixed Polarizer Ellipsometer (RACFPE);

j. Rotating Polarizer and Compensator, Fixed Analyzer (RPCFAE);

k. Rotating Analyzer, Fixed Polarizer and Compensator Ellipsometer (RAFPCE);

l. Rotating Polarizer, Fixed Analyzer and Compensator Ellipsometer (RPFACE);

m. Rotating Compensator, Fixed Analyzer and Polarizer Ellipsometer (RCFAPE);

(Note that similar identifying descriptions also apply to Polarimeter and the like Systems).

However, for the purposes of the present invention it is not necessary to describe each above listed system in detail. The present invention, while applicable to essentially any Ellipsometer or Polarizer and the like System, is focused upon the simultaneous production of a plurality of measureable Orders of essentially single wavelength polarized beams of light from a polychromatic beam of light, which polychromatic beam of light has been caused to interact with a Sample System. (Note that a Dispersive Optics actually provides a continuous spectrum of spacially separated wavelengths which are present in a Polarized Source Light Beam. It is convenient, however, to view said spectrum as a multiplicity of essentially single wavelength polarized beams of light. Such an approach has particular relevance where, because of size and placement, a Detector Element intercepts a relatively narrow band of said wavelengths centered about some wavelength in a physically realized system).

Continuing, the Woollam et al. U.S. Pat. No. 359 Patent identified above, presents a system of two Diffraction Gratings toward the end goal of the present invention, wherein a polarized beam of light Diffracted by one Diffraction Grating is caused to impinge upon another and provide a second spectrum of wavelengths. There exists, however, need for an improved approach to simultaneously providing a plurality of "Orders" per se. of polarized essentially single wavelength polarized beams of light. The reason for this is that simultaneous analysis of information in a plurality of essentially single wavelength polarized beams of light, which essentially single wavelength polarized beams of light are derived from a polychromatic polarized beam of light, which polarized polychromatic polarized beam of light has been caused to interact with a Sample System, allows more convenient characterization of more complex Sample Systems.

A paper titled "Division-Of-Amplitude Photopolarimeter Based on Conical Diffraction For a Metallic Grating" by Azzam, in Applied Optics, Vol 31, No. 19, 1 Jul. 1992 and U.S. Pat. No. 5,337,146 are also noted. The purpose of the System and Method of Use described in said references is to allow simultaneous measurement of all four Stokes Parameters of a Beam of Light. The System involved is a Gratting which serves to provide Four Orders, each of which must be intercepted, possibly by a Detector Array. While the present invention System is to some extent similar to that alluded to in said Azzam references, it is to be appreciated that the Purpose to which the present invention System speaks, and the Method of Use thereof are very different than that described by Azzam. As well, the Azzam System, while providing for Polarization of wavelengths in certain Orders, does not provide for the filtering-out of stray light or of overlapping portions of adjacent Orders to provide wavelengths of an Order free of any masking influence of wavelengths present in an adjacent Order. The present invention provides that multiple, element filters be present, which, in the context of spectroscopic ellipsometer or polarimeters and the like has not, to the inventor's knowledge, been previously known.

The present invention then, as taught supra in this Disclosure, is a multiple "Order" producing Dispersive Optics system and method of application thereof, for use in providing a multiplicity of essentially single wavelength polarized beams of light, in combination with Ellipsometers and/or Polarimeters and the like. The purpose thereof is to allow simultaneous detection and analysis of closely situated wavelengths, by interception thereof in different Multiple Order producing Dispersive Optics produced Orders, which closely situated wavelengths can not be simultaneously detected in a single Order because of Detector Element finite dimension limitations.

DISCLOSURE OF THE INVENTION

The present invention is a Multiple "Order" Producing Dispersive Optics System in combination with a Spectroscopic Ellipsometer or Polarimeter and the like System, and Method of Application thereof.

As described in the Background Section, the ability to simultaneously produce a polychromatic beam of light, cause it to interact with a Sample System, and then analyze a multiplicity of essentially single wavelength polarized beams of light derived therefrom present in a plurality of "Orders", in an Ellipsometer or Polarimeter and the like system, enables convenient analysis and evaluation of defining coefficients for complex Sample Systems, (e.g. such as film thickness, refractive index and extinction coefficient or dielectric function real and imaginary components etc., of multiple layer thin films atop sample substrates). The present invention is focused upon the use of Multiple "Order" producing Dispersive Optics systems in Ellipsometer or Polarimeter and the like systems, to produce said multiplicity of essentially single wavelength polarized beams of light in a plurality of "Orders", from a polychromatic polarized beam of light which is caused to interact with a Sample System.

A primary example of the present invention Multiple "Order" Producing Dispersive Optics System is a Diffraction Grating, which Diffraction Grating Diffracts a polychromatic polarized beam of light into a multiplicity of essentially single wavelength polarized beams of light, when said polarized polychromatic beam of light is caused to impinge thereupon at some predetermined angle. (Note, a Diffraction Grating is typically defined as a repetitive array of diffracting elements, either aperatures or obsticals, which has the effect of producing periodic alterations in phase, amplitude, or both in an emergent wave, by the effect thereof on an incident wave. Alternating Opague-Transparent Multiple-slit configurations can constitute "Transmission Amplitude Gratings", whereas essentially Fully Transparent Gratings with Parallel Lines etches therein can constitute "Transmission Phase Gatings". Opague Gratings with Lines etched therein similarly can be considered as Reflection Phase Gratings).

The Equation which describes the formation of a plurality of "Orders" by a Grating, from an incident polychromatic Beam of Light, each of which "Orders" contains a continuium of a multiplicity of essentially single wavelength polarized beams of light is:

$$a*\mathrm{SIN}\ (THETAm)=m*LAMBDA;$$

where "a" is the spacing of Grating Lines, "THETAm" is the angle at which a particular wavelength projects, "m" is the Order, (First, Second etc.), and "LAMBDA" is a wavelength.

If a polychromatic beam of polarized light is incident upon a Diffraction Grating along other than a "Normal" thereto, the governing Equation is:

$$a*(\mathrm{SIN}\ (THETAm)-\mathrm{SIN}\ (THETAi))=m*LAMBDA;$$

where "THETAi" is the angle of incidence and the other symbols were defined above. Note that if "THETAm" equals "THETAi" the "Zeroth Order" results. While energy present in a "Zeroth Order" is not dispersed into a continuium of diffracted essentially single wavelengths, said "Zeroth Order" energy can at times be utilized, (for instance, where it reflects from the surface of a Diffraction Gratting in a direction other than coincident with the incident Beam of Light). It is noted that use of a "Blazed" Reflection Phase Grating" can shift energy from a "Zeroth Order" and into higher more useful "Orders". Blazed Gratings have nonsymmetrical Grating etchings, and involve a "Blaze Angle". This is described in "HECHT OPTICS, 2nd Edition, Addison-Wesley, 1987, which reference is incorporated herein by reference. Also, filters can be applied to the Zeroth-Order to provide specific wavelength(s) therein to a detector thereof.

To assure that the present invention is clearly disclosed, it is to be understood that, as used in this Disclosure, the term "Order" refers to a "Full Range" continuium of Diffracted Essentially Single Wavelength Polarized Beams of Light. When present, Multiple "Orders" are spacially separated from one another, but can "Overlap" one another. (Note that Filters are utilized to separate such "Overlapping Orders" and to essentially eliminate stray light entering a Detector Element). With this in mind it can be understood that a present invention Dispersive Optics provides a plurality of "Full Range" "Orders" of essentially single wavelength polarized beams of light, each of which spacially separated "Orders" of essentially single wavelength polarized beams of light contains a "Full Range" continuium of wavelengths between some lower and some upper wavelength limit, when a source polychromatic polarized beam of light is caused to impinge thereupon. The wavelength content of an "Order" being limited only by the wavelength of a Light Source which provides a beam of light to an "Order" producing Dispersion Optics.

The utility of the presence of a number of such "Orders" of spacially separated essentially single wavelength polarized beams of light is based in the fact that physical size limitations prevent a Photodetector Array from providing a Detector Element therein at an appropriate location at which to intercept every desired essentially single wavelength polarized beam of light in a single Order. That is, in a single "Order", the detecting of one essentially single wavelength polarized beam of light prevents detecting a closely situated, (in space), essentially single wavelength polarized beam of light, because the presence of one Detector Element positioned to intercept one essentially single wavelength polarized beam of light prevents the presence of another Detector Element being simultaneously situated so as to be able to detect said closely situated essentially single wavelength polarized beam of light. However, a polarized beam of light of said closely situated essentially single wavelength, being also present in another "Order", can be simultaneously accessed therein by a Detector Element which can be positioned so as to Detect it. That is, if an essentially single wavelength polarized beam of light can not be accessed in one "Order" because of physical Detector Element obstruction in the space thereof, it very likely can be accessed in another spacially offset "Order".

The present invention system is then a Multiple-Order Producing Dispersive Optics in combination with an Ellipsometer or Polarimeter and the like system. In addition, and importantly, filters are present to eliminate the effects of stray light and the effect of wavelengths in one Order on an adjacent Order, in regions of overlap therebetween. The Method of Application of the present invention involves utilization of said Multiple "Orders" to allow positioning Detector Elements so as to access desired essentially single wavelength polarized beams of light of closely situated Wavelengths.

The present invention will be better understood by reference to the Detailed Description Section in this Disclosure, in conjunction with the accompanying Drawings.

SUMMARY OF THE INVENTION

It is therefore a purpose of the present invention to provide a multiple order producing dispersive optics system for application in ellipsometer or polarimeter and the like systems.

It is another purpose of the present invention to teach that the present invention can be practiced in conjunction with essentially any ellipsometer or polarimeter and the like system.

It is yet another purpose of the present invention to teach that, in use, closely situated essentially single wavelength polarized beams of light can be detected in various orders, thereby allowing simultaneous detection thereof, where physical constraints would prevent such were but a single order available.

It is an additional purpose of the present invention to teach that, in use, filters should be applied to reduce stray light and separate the effects of adjacent orders in regions of overlap therebetween.

It another purpose yet, of the present invention, to teach that suitable dispersive optics for the practice thereof, include diffraction gratings, (reflective, transmittive, lined, Blazed, Hologram, slited etc.), appropriate prisms and functional equivalents.

DETAILED DESCRIPTION

Figure 1A:
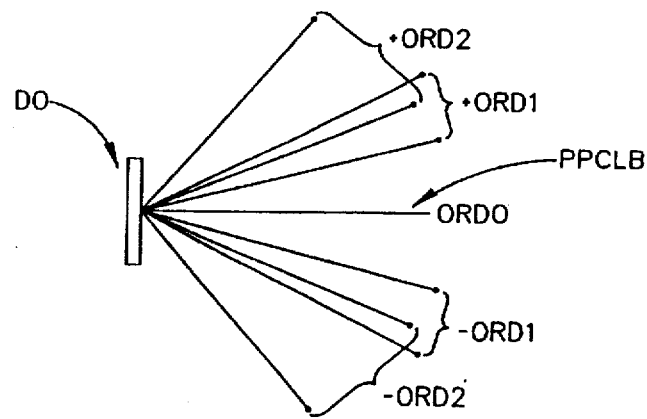
FIG. 1a shows a Dispersive Optics (DO) of the present invention accompanied by a plurality of "Orders" of polarized essentially single wavelength beams of light.

Turning now the Drawings, there is shown in FIG. 1a a Dispersive Optics (DO) upon which a Polychromatic Light Beam (PPCLB), (shown superimposed on a zero Order (ORD0) reflection), is impinged, with the result being formation of a plurality of higher "Orders" (−ORD1, −ORD2, +ORD1 and +ORD2). Each higher "Order" being comprised of a continuium of wavelengths, conveniently viewed as a multiplicity of essentially single wavelength beams of light, each of which "Orders" has essentially equal lower and upper wavelength boundaries. The angular spacial separation spread, however, between contained essentially single wavelength beams of light in the higher Orders being typically larger than in lower Orders. Note that the higher Orders and lower Orders overlap, (ie. +ORD1 and +ORD2 overlap and −ORD1 and −ORD2 overlap).

Figure 1B:
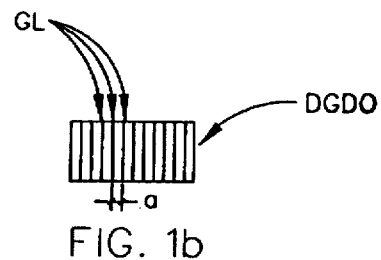
FIG. 1b demonstrates a Lined Grating.

FIG. 1b shows a "Gratting-Lined" (GL) Dispersive Optics Diffraction Gratting which could be applied to produce the "Orders" identified in FIG. 1a. In use a (PPCLB) is caused to be incident upon the surface of the Diffraction Gratting Dispersive Optics (DGDO). Typically Grating Lines (GL's) are separated by a distance "a", which is the "Groove Width". The spacial separation of wavelengths in an "Order" being described by the equation:

$$a*SIN(THETA)=N*LAMBDA,$$

where THETA is the angular spread of a Wavelength in an "Order" of number "N", (e.g. 1 or 2), and LAMBDA is wavelength.

Figure 1C:
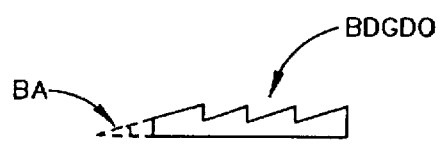
FIG. 1c demonstrates a Blazed Grating Line configuration.
Figure 1D:
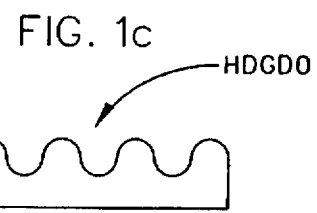
FIG. 1d demonstrates a Holographic Grating Line configuration.

FIG. 1c demonstractes a "Blazed" Diffraction Grating Dispersion Optics (BDGDO), with "Blazed Grating Lines". Note the Blazed Angle (BA). Gratings of this type, as opposed to those which provide simple symetrically etched lines, can shift energy from a "Zeroth Order" into higher Orders. FIG. 1d shows a "Hologrpahic" Diffraction Gratting Dispersion Optics (HDGDO), in which the upper surface of present Diffraction Gratting Lines is of a repeating COSINE shape.

Figure 2:
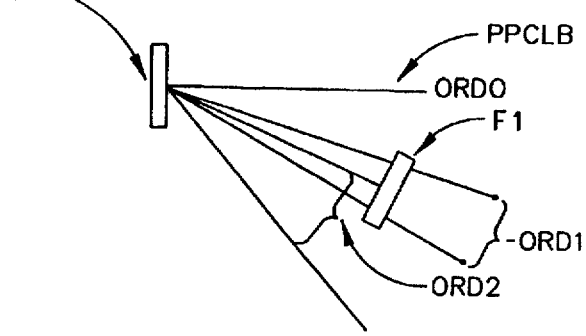
FIG. 2 shows the Dispersive Optics (DO) of the present invention accompanied by a two "Orders" of polarized essentially single wavelength beams of light.

FIG. 2 shows the Dispersive Optics (DO) of FIG. 1, with two of the overlapping "Orders", (+ORD1 and +ORD2), shown in FIG. 1 presented. Also shown is a Filter (F1) which serves to remove the higher Order (−ORD2) longer wavelength contribution leaving only shorter wavelengths from Order (−ORD1) present past said Filter (F1). While the intensity associated with a wavelength in a Second "Order" (ie. −ORD2 or +ORD2), is generally only approximately one-tenth (1/10) that associated with a First (−ORD1 or +ORD1), in the range of overlap between "Orders", (e.g. between −ORD1 and −ORD2 or between +ORD1 and +ORD2), the effect of a Second "Order" longer wavelength on the ability to measure a First "Order" shorter wavelength is not negligible, and typically must be filtered away to allow accurate First Order shorter wavelength Intensity measurements to be achieved.

Figure 3:
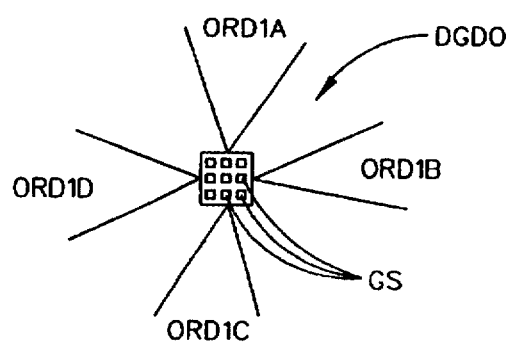
FIG. 3 shows a Grating which can provide four First Orders.

FIG. 3 shows that a Diffraction Gratting Dispersive Optics (DGDO) comprised of a Diffraction Gratting etched to have a multiplicity of "Grating Squares" (GS) thereon, and which can be utilized to provide four (4) First Orders (e.g. ORD1A, ORD1B, ORD1C and ORD1D). It is noted however, that the energy which is present in the two First Orders (−ORD1 and +ORD1) of FIGS. 1 and 2, will be spread into four (4) First Orders as shown in FIG. 3. This means that the intensity in an Order where a greater number thereof are formed, will be less than in a case wherein a fewer number of Orders are formed. Said intensity can be sufficient, however, to allow use of four such First Orders. Other Diffraction Gratting Geometries can provide other numbers of such First Orders.

Figure 4:
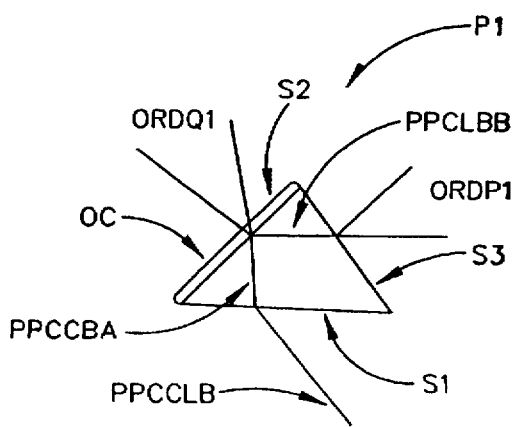
FIG. 4 shows use of a special Prism to provide two spacially spread continuiums of essentially single wavelength polarized beams of light.

FIG. 4 shows a Prism (P1) which has three Surfaces (S1), (S2) and (S3). Surface (S2) is shown with a partially reflective coating (OC) thereon. A Polarized Polychromatic Light Beam (PPCCLB) is shown as incident on one surface (S1) thereof, and refracted to become (PPCCBA), which refracted beam is partially tramsmitted, and partially reflected, as (PPCLBB) at Surface (S2). Emerging from Surfaces (S2) and (S3) are Orders (ORDQ1) and (ORDP1). Said Orders contain essentially equivalent wavelength spectrums and spacial spread of wavelengths therein. The Intensities of wavelengths in the two Orders might be somewhat different depending on reflection/transmission efficiency and on longer additional pathway (PPCBA+PPCLBB) and attenuation losses etc. of the (ORDP1) Order forming beam as comparrred to the (PPCCBA) pathways regarding the (ORDQ1) beam, however, both said Orders can be simultaneoulsy intercepted and utilized.

Figure 5:
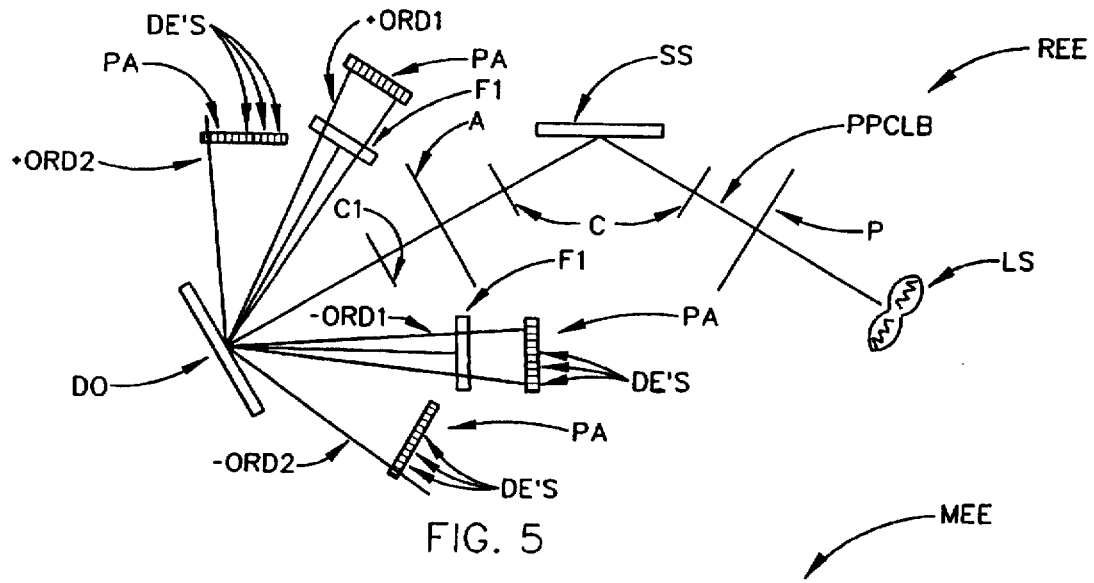
FIG. 5 shows the Dispersive Optics (DO) of the present invention accompanied by two "Orders" of polarized essentially single wavelength beams of light, in the context of a Rotating Element Ellipsometer (REE) System.

FIG. 5, shows a present invention Multiple Order producing Dispersive Optics in combination with elements of a Rotatable or Rotating Element Ellipsometer (REE); said elements comprising a Light Source (LS), a Polarizer (P), perhaps Compensators (C), and an Analyzer (A), as well as Photodetector Arrays (PA's), each of which Photodetector Arrays (PA's) contains Detector Elements (DE's). In use said Light Source (LS) is caused to provide a beam of polychromatic light, which beam of polychromatic light is caused to become "Polarized" by passage through the Polarizer (P) and become a Polarized Polychromatic Light Beam (PPCLB). Interaction with a Sample System (SS), serves to alter the Polarization State of said beam of Polarized Polychromatic Light Beam (PPCLB) in a manner which identifies physical and optical properties thereof. Said Polarized Polychromatic Light Beam (PPCLB) is shown to, preferrably without additional focusing thereof, interact with said Dispersive Optics (DO) and form a plurality of "Orders" (ie. −ORD2, −ORD1 and +ORD1, +ORD2), of Essentially Single Wavelength Polarized Beams of Light, each said "Order" being intercepted by Photodetector Arrays (PA's). Note that a Filter (F1) is present with respect to both Orders (−ORD1) and (+ORD1) to separate out the effects of (−ORD2) and (+ORD2) respectively, prior to said (−ORD1) and (+ORD1) being intercepted by said (PA's). It is also to be noted that the Photodetector Arrays (PA's) each contain a multiplicity of Detector Elements (DE's) which can be utilized to produce a signal which represents an essentially single wavelength beam of light. As well, it is to be noted that the Polarizer (P), Analyzer (A) and Compensators (C) can be variously Stationary, Rotatable and Rotating.

Also note in FIG. 5, that the Photodetector Arrays (PA's) poistioned to intercept essentially single wavelength polarized light beams in the Second Order, (+ORD2) and (−ORD2), are shown oriented closer to the Dispersive Optice (DO), than Photodetector Arrays (PA's) associated with interception of essentially single wavelength beams of light in First Orders (+ORD1) and (−ORD1). This is to indicate that the angular spread between essentially single wavelength beams of light in Second Orders is generally greater than that in First Orders. Generally, one can adjust the distance from a Dispersive Optics (DO) at which a Photodetector Array (PA) is located, so as to intercept a desired range of essentially single wavelength light beams.

Figure 6:
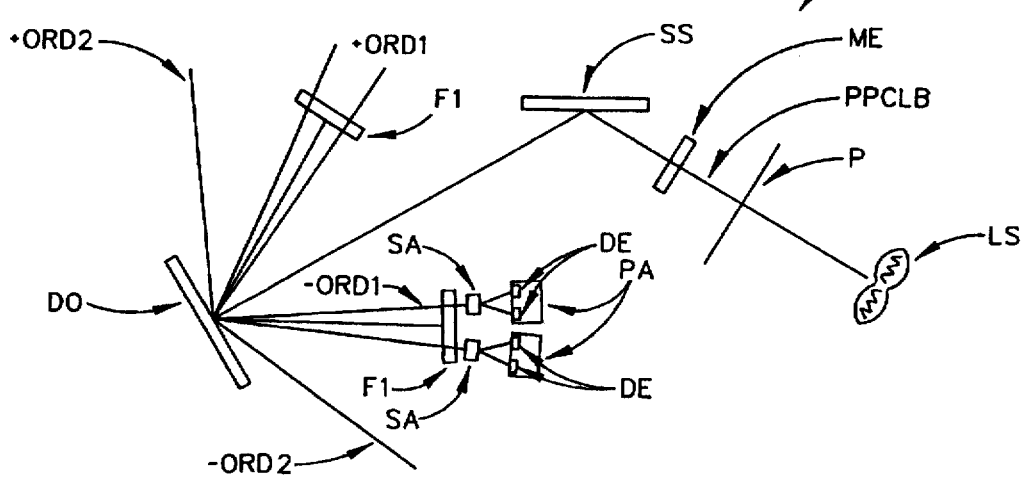
FIG. 6 shows the Dispersive Optics (DO) of the present invention accompanied by two "Orders" of polarized essentially single wavelength beams of light, in the context of a Modulator Element Ellipsometer (MEE) System.
Figure 8:
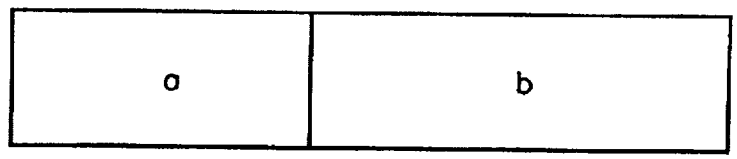
FIG. 8 shows that a Filter (F1) can be comprised of Multiple Sections.

Turning to FIG. 6, there is shown the Multiple Order producing Dispersive Optics (DO) of FIG. 1 with two "Orders", (−ORD2, −ORD1 and +ORD1, +ORD2) shown in FIG. 1 also shown, in combination with elements of a Modulation Element Ellipsometer (MEE) System; said elements comprising a Light Source (LS), a Polarizer (P), and a Modulation Element (ME), as well as Split Analyzers (SA's) and Photodetector Arrays (PA's), each of which Photodetector Arrays (PA's) contains Detector Elements (DE's). (It is to be understood that some Modulation Element Ellipsometers subject only one quadrature component to analysis, hence, only one beam quadrature component from the Split Analyzers (SA) is intercepted). Similar to the case of a (REE) System described infra, in use said Light Source (LS) is caused to provide a beam of polychromatic light, which beam of polychromatic light is caused to become "Polarized" by passage through the Polarizer (P) and become a Polarized Polychromatic Light Beam (PPCLB). However, in the present case said (PPCLB) is then subjected to a Modulation Element (ME) which serves to Polarization State Modulate the Polarized Polychromatic Light Beam (PPCLB). After interaction with a Sample System (SS), which interaction serves to alter the Polarization State of said Modulated Polarized Polychromatic Light Beam (PPCLB) in a manner which identifies physical and optical properties thereof, said Modulated Polarized Polychromatic Light Beam (PPCLB) is shown to interact with said Dispersive Optics (DO) and form a plurality of "Orders", (−ORD2, −ORD1, +ORD1, +ORD2), each comprised of a multiplicity of Essentially Single Wavelength Polarized Beams of Light. Said Order (−ORD1) is shown as intercepted by Photodetector Arrays (PA's), after passing through Filter (F1) to remove the effects of (−ORD2), after which each essentially single wavelength beam of light is caused to be split into its Quadrature Components, (such as the "P" and "S" Components when they are referred to the Sample System), by said Split Analyzers (SA's). Note, FIG. 8 demonstrates that the Filter (F1) can be of multiple Section, (a and b), construction, wherein each Section (a and b) has different filtering characteristics, as demonstrated by FIGS. 9 and 10 respectively. In use, the Filter (F1) Section "a", for instance, serves to prevent stray light from entering a Detector Element, and "masking" passed ultraviolet wavelength light intensity. That is it allows only ultraviolet light to pass therethrough. Section "b", for instance, serves to eliminate adjacent "Order" wavelengths from an "Order" of interest. That is, for instance, it passes wavelengths of four-hundred (400) to five-hundred (500) nanometers while blocking stray ultraviolet and infrared wavelengths. Filter (F1) is an important element of the present invention.

It is to be noted that the Photodetector Arrays (PA's) each contain Detector Elements (DE's) which can be utilized to produce signals which represent an essentially single wavelength beam of light. It is to be noted that the Polarizer (P) and Analyzer (A) can be variously Stationary, Rotatable and Rotating. Although not shown to reduce Drawing clutter, similar Phodetector Arrays (PA) can be applied to intercept the (+ORD1) "Order" after essentially single wavelength beams of light in said (+ORD1) "Order" pass through associated Filter (F1).

The present invention then simultaneously utilizes a plurality of "Orders", each of which contains a continuium of essentially single wavelength beams of light to allow simultaneous measurement of more essentially single wavelength beams of light than possible if only one "Order" were available. Note that the present invention requires the presence of only one (1) Dispersive Optics (DO) to effect said result. While the production of a plurality of "Orders" is attended by a reduction in the amount of energy present in each, hence, in the Intensity associated with an essentially single wavelength beam therein, the benefits of haveing a plurality of wavelength spectrums to intercept and analyze allows simultaneous analysis of many more wavelengths than is possible if only one "Order" is available or utilized.

It should also be understood that it is, in some circumstances, typical J.A. Woolam Co. Inc. practice to subject a beam of light exiting a Rotating Analyzer in an (RAE), to, for instance, a retarder, or a depolarizing element, (demonstrated in FIG. 5 by Compensator C1), so that a Diffracted Spectrum of essentially single wavelength beams of light in an Order, are not any longer at all Linearly Polarized, and if at all Polarized, essentially Circularly Polarized. This is discussed in Co-pending applications Ser. Nos. 08/265,325 and 08/339,834. (Note, Essentially circularly polarization refers to elliptical polarization in which magnitudes of "P" and "S" components are not exactly equal, and/or in which the phase angle therebetween is not exactly ninety (90) degrees, but in which said values are close to equal and/or ninety (90) degrees respectively). This is done because Detector Elements typically display Polarization Dependence Sensitivity (PDS). That is, said Detector Elements respond differently to beams of light of equal Intensity but which have different states of polarization. Said Polarization Dependence Sensitivity (PDS) is minimized when unpolarized light, or essentially circularly light, is presented thereto. For this reason, the Claims include no designation regarding the polarization state of light entering a Detector Element, and light in any state of polarization, or unpolarized light, can be present, within the scope thereof.

It is also noted that a specific embodiment of a Spectroscopic Ellipsometer System is taught in now U.S. Pat. No. 5,373,359 to Woollam et al., from which the present Application Continues. Said embodiment being, essentially, a spectroscopic ellipsometer for use in sensing characteristics of a sample substrate system comprising a light source, a polarization state generator, an analyzer and a dispersion optics positioned so as to receive a beam of polychromatic light which passes through the analyzer without further focusing after said beam of polychromatic light, which originates in said light source, reflects from said sample substrate system; wherein said dispersive optics directs incident polychromatic light onto a photodetector array at a predetermined angle with respect to a normal to said dispersive optics, with a precision of at least plus or minus one-half degree. Said precision being achieved by rotation of said dispersive optics, as shown in FIGS. 1, 2a, 5 and 6 in this present Disclosure, about an appropriate axis. It is specifically noted that the Dispersive Optics in such a system, whether multiple Orders are produced thereby, and whether or not multiple Orders are utilized or not, can comprise Diffraction Gratings and/or Prisms and/or functional equivalents.

It is to be understood that the Terminology "Polarization State" refers to a set of "Magnitude Ratio and Phase Angle" values of a Polarized Beam of Light. See the Background Section of this Disclosure for a description of "P" and "S" Quadrature Components, for instance.

It is also to be understood that the terminology "Light Beam" has been used. This is to be taken to generally refer to electromagnetic radiation of any wavelength.

Figure 7:
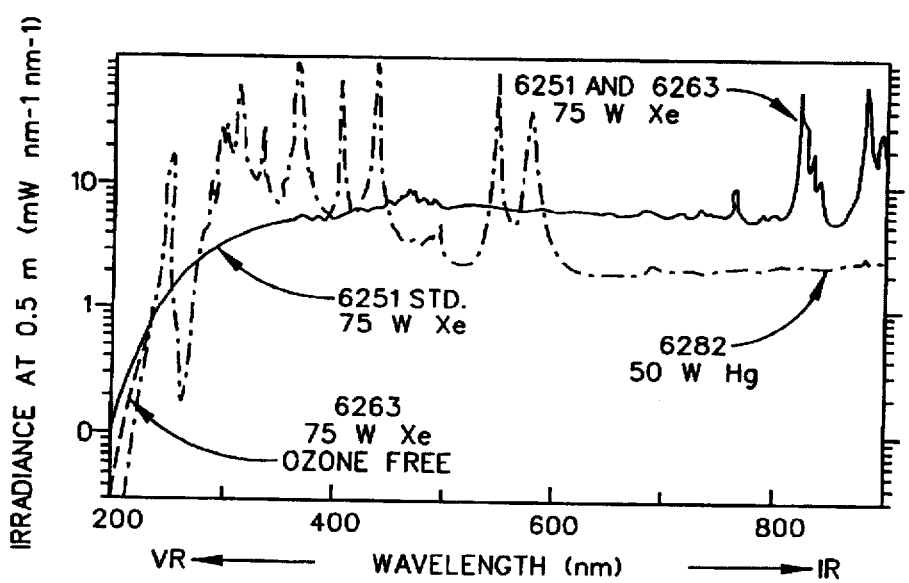
FIG. 7 shows the wavelength content of Xenon, and Mercury Vapor, Light Sources.

As well, it is to be understood that an "Order" will contain all wavelengths present in a beam of light incident upon an "Order" forming Dispersive Optics. This can include from essentially zero to essentially infinitely long. (However, if the source of said incident light is missing certain wavelengths, they, of course, are not to be expected to appear in a dispersed "Order". FIG. 7 shows plots of wavelengths present in, for instance, light provided by Mercury and Xenon lamps available from the "Oriel" Corpoaration. When said lamps are used as a Source of light, wavelengths present can be expected to be available in dispersed Orders, in relative intensities proportional to that provided by said Sources. A particularly suitable Light Source is a Xenon Lamp which provides polychromatic light with wavelengths in the range of from 0.25 to 1.7 microns. A quartz-tungsten halogen lamp can also be utilized if only wavelengths above approximately 0.4 micron are utilized.

It is to be understood that while an "Order" contains a continuium of wavelengths limited only by the content of a Light Source, it can be viewed as containing a spectrum comprising a multiplicity of essentially single wavelength beams of light. This approach is helpful when considering how a Photodetector Array (PA) intercepts an "Order", and was adopted herein. Finite dimension individual Detector elements (DE's) in a Photodetector Array (PA) are physically positioned to intercept a small band of wavelengths centered at an essentially single wavelength, which small band of wavelengths comprise an essentially single wavelength beam of light.

It is also disclosed that suitable Photodetector Arrays are available from E. G and G. Judson, 221 Commerce Dr., Montgomeryville, Pa., 18936, under the Product Number PDA38. Said chip containing the Photodiodes is approximately 15.2 millimeters wide, 51 millimeters long, 3 millimeters deep. The active area of the Photodiodes is approximately 3.8 square millimeters, with spacing between Detector Elements being a millimeter. It is noted however, that photodetector Arrays with Detector Element spacing as small as thirty (30) microns are possible and within the scope of the present invention.

Suitable Detector Elements are also available from Electro-Optical Systems, Inc. at Greenway Technology Park, 1000 Nutt Road, Pheonixville, Pa., 19460.

Figure 9:
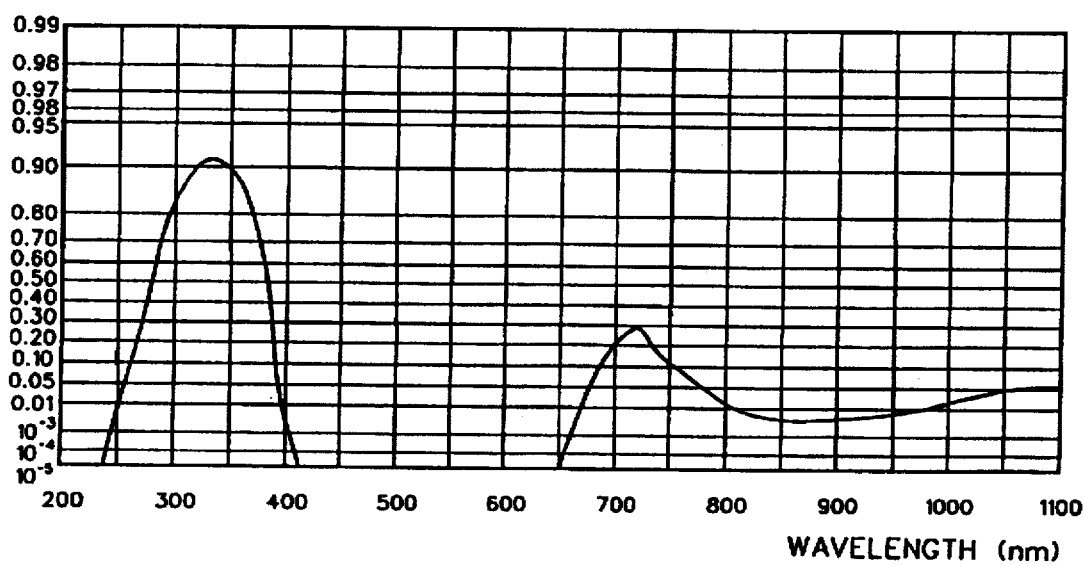
FIG. 9 demonstrates a filter (F1) section characteristic.
Figure 10:
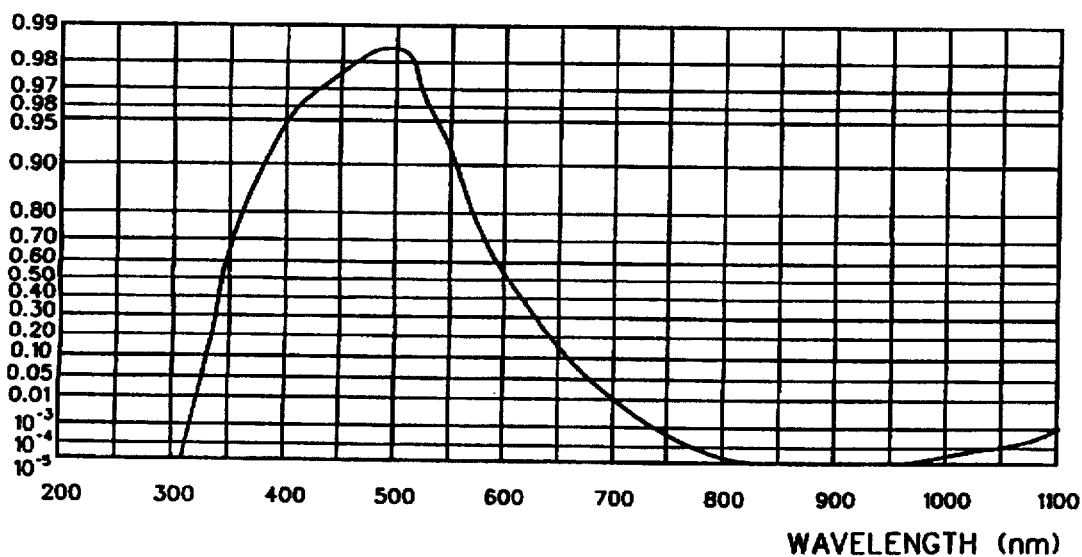
FIG. 10 demonstrates a filter (F1) section characteristic.

It is noted that the Plots in FIGS. 9 and 10 are adapted from the materials of Schott Glass Technologies Inc.

A suitable Dispersive Optics is a pivotally mounted Diffraction Grating which allows adjusting the angle at which a polychromatic beam of light approaches thereto, with respect to a normal a the surface thereof, is adjustable, preferrably, to within plus or minus one-half (0.5) a degree. Said suitable Diffraction Grating also provides a spectrum of essentially single wavelength beams of light with wavelengths in the range of from 0.25 to 1.0+ microns.

Having hereby disclosed the subject matter of the present invention, it should be obvious that many modfications, substitutions, and variations of the present invention are possible in light of the teachings. It is to be understood that the invention can be practiced other than as specifically described, and should be limited in breadth and scope only by the Claims.

We claim:

1. A multiple order producing dispersive optics system in combination with a system selected from the group consisting of a spectroscopic ellipsometer system and a spectroscopic polarimeter system, which multiple order producing dispersive optics system produces a plurality of orders, which orders are essentially spacially offset from one another, when a polychromatic beam of light is caused to impinge upon said dispersive optics system, each said produced order comprising an essentially continuous spectrum of spacially separated light beams of essentially single wavelengths, many of said essentially single wavelengths being present in two or more produced orders; such that in use first and second multiplicities of essentially single wavelength beams of light from first and second produced orders are simultaneously intercepted by, respectively, first and second photo detector arrays, thereby enabling the simultaneous accessing of a first multiplicity of essentially single wavelengths by said first photo detector array and a second multiplicity of essentially single wavelengths by said second photo detector array, each of which first and second multiplicities of essentially single wavelengths intercepted by said first and second photo detector arrays, respectively, includes specific first and second essentially single wavelength beams of light, said specific first and second essentially single wavelength beams of light being simultaneously intercepted by specific detector elements in said first and second photo detector arrays respectively, even where light beams of said specific first and second essentially single wavelengths are spacially situated to close to one another in a single produced order for separate photo detector array detector elements in a single photo detector array which intercepts said single order, to, simultaneously, access beams of light of both said specific first and second essentially single wavelengths, separately.

2. A multiple order producing dispersive optics system as in claim 1, which comprises a diffraction grating, and in which filters are present to allow passage of wavelengths in one produced order, and not wavelengths in an adjacent spacially overlapping produced order, to a photo detector array, said filters further serving to prevent stray light from accessing said detector elements.

3. A multiple order producing dispersive optics system as in claim 2, in which said grating is selected from the group consisting of a "lined", a "blazed", and a "holographic" geometry, said lined geometry consisting essentially of symetrical alternating lines with depressions therebetween, and said blazed geometry consisting of alternating ramp shaped lines with depressions therebetween, and said holographic geometry consisting of continuous cosine shaped lines and depressions.

4. A multiple order producing dispersive optics system as in claim 1, which comprises a Prism.

5. A multiple order producing dispersive optics system as in claim 1, in which the system selected from the group consisting of a spectroscopic ellipsometer system and a spectroscopic polarimeter system, is comprised of elements selected from the group consisting of:

stationary polarizers;

stationary compensators;

stationary analyzers;

rotatable polarizers;

rotatable compensators;

rotatable analyzers;

rotating polarizers;

rotating compensators;

rotating analyzers;

modulator elements.

6. A multiple order producing dispersive optics system as in claim 5 in which said system selected from the group consisting of a spectroscopic ellipsometer system and a spectroscopic polarimeter system comprises a rotatable/rotating analyzer and is a rotatable/rotating analyzer system.

7. A multiple order producing dispersive optics system as in claim 5 in which said system selected from the group consisting of a spectroscopic ellipsometer system and a spectroscopic polarimeter system comprises a rotatable/rotating polarizer and is a rotatable/rotating polarizer system.

8. A multiple order producing dispersive optics system as in claim 5 in which said system selected from the group consisting of a spectroscopic ellipsometer system and a spectroscopic polarimeter system comprises a rotatable/rotating compensator and is a rotatable/rotating compensator system.

9. A multiple order producing dispersive optics system as in claim 5 in which said system selected from the group consisting of a spectroscopic ellipsometer system and a spectroscopic polarimeter comprises a modulator element, and is a modulation element ellipsometer system.

10. A method of providing simultaneous access to two or more essentially single wavelengths of light which, in a diffracted single order essentially continuous spectrum of wavelengths can be spacially situated to close to one another for available photodetector elements in a single order intercepting photo detector array to simultaneously separately detect, comprising the steps of:

a. providing a multiple order producing dispersive optics system in combination with a system selected from the group consisting of a spectroscopic ellipsometer system and a spectroscopic polarimeter system, which multiple order producing dispersive optics system produces a plurality of orders, which orders are essentially spacially offset from one another, when a polychromatic beam of light is caused to impinge upon said dispersive optics system, each said produced order comprising an essentially continuous spectrum of spacially separated light beams of essentially single wavelengths, many of said essentially single wavelengths being present in two or more produced orders; such that in use first and second multiplicities of essentially single wavelength beams of light from first and second produced orders are simultaneously intercepted by, respectively, first and second photo detector arrays, thereby enabling the simultaneous accessing of a first multiplicity of essentially single wavelengths by said first photo detector array and a second multiplicity of essentially single wavelengths by said second photo detector array, each of which first and second multiplicities of essentially single wavelengths intercepted by said first and second photo detector arrays, respectively, includes specific first and second essentially single wavelength beams of light, said specific first and second essentially single wavelength beams of light being simultaneously intercepted by specific detector elements in said first and second photo detector arrays respectively, even where light beams of said specific first and second essentially single wavelengths are spacially situated to close to one another in a single produced order for separate photo detector array detector elements in a single photo detector array which intercepts said single order, to, simultaneously, access beams of light of both said specific first and second essentially single wavelengths, separately;

b. causing a polychromatic beam of light produced in said system selected from the group consisting of a spectroscopic ellipsometer system and a spectroscopic polarimeter system, to interact with a sample system, impinge upon said multiple order producing dispersive optics and produce at least two orders, each of said produced orders comprising an essentially continuous spectrum of spacially separated essentially single wavelengths in a range of wavelengths which is similar in at least two orders;

c. accessing desired first and second essentially single wavelength beams of light by detector elements in, respectively, said first and second produced order intercepting photo detector arrays.

11. A method of providing access to closely situated essentially single wavelengths which also reduces polarization-dependence sensitivity of dispersive optics in a system selected from the group consisting of a rotating analyzer ellipsometer and a rotating analyzer polarimeter system, comprising the steps of:

a. providing a system selected from the group consisting of a rotating analyzer ellipsometer and a rotating analyzer polarimeter system comprising:
   a. a light source;
   b. a polarization state generator;
   c. a rotating analyzer;
   d. a compensator;
   e. a dispersive optics; and
   f. photodetector systems;

such that, during use, a polychromatic beam of light from said light source is caused to pass through said polarization state generator and is then caused to interact with a substrate system, thereby becoming typically elliptically polarized; and such that said typically elliptically polarized polychromatic beam of light is then caused to pass through said rotating analyzer and become essentially linearly polarized, which essentially linearly polarized polychromatic beam of light emerging from said rotating analyzer is then caused to pass through said compensator, such that said linearly polarized beam of light which exits said rotating analyzer is caused, by passage through said compensator, to become other than linearly polarized, said other than linearly polarized polychromatic beam of light which emerges from said compensator being then caused to interact with said dispersive optics and emerge therefrom as a plurality of produced orders, each of said produced orders comprising an essentially continuous spectrum of essentially single wavelength beams of light which enter detector elements of photodetector systems which intercept said orders, for analysis therein;

b. causing a polychromatic beam of light to emerge from said light source, proceed through said polarization state generator, interact with said substrate system, proceed through said rotating analyzer and said compensator after interacting with said substrate system, then interact with said dispersive optics such that a plurality of orders, each of which comprises an essentially continuous spectrum of essentially single wavelengths, are produced; and c. simultaneously accessing desired essentially single wavelength beams of light in at least two of said produced orders by detector elements in said photo detector arrays which intercept said produced orders.

12. A multiple order producing dispersive optics system in combination with a system selected from the group consisting of a spectroscopic ellipsometer system and a spectroscopic polarimeter system, which multiple order producing dispersive optics system produces a plurality of orders, which orders are essentially spacially offset from one another, when a polychromatic beam of light is caused to impinge upon said dispersive optics system, each said produced order comprising an essentially continuous spectrum of spacially separated light beams of essentially single wavelengths, many of said essentially single wavelengths being present in two or more produced orders; such that in use first and second multiplicities of essentially single wavelength beams of light from first and second produced orders are simultaneously intercepted by, respectively, first and second photo detector arrays, thereby enabling the simultaneous accessing of a first multiplicity of essentially single wavelengths by said first photo detector array and a second multiplicity of essentially single wavelengths by said second photo detector array, each of which first and second multiplicities of essentially single wavelengths intercepted by said first and second photo detector arrays, respectively, includes specific first and second essentially single wavelength beams of light, said specific first and second essentially single wavelength beams of light being simultaneously intercepted by specific detector elements in said first and second photo detector arrays respectively, even where light beams of said specific first and second essentially single wavelengths are spacially situated to close to one another in a single produced order for separate photo detector array detector elements in a single photo detector array which intercepts said single order, to, simultaneously, access beams of light of both said specific first and second essentially single wavelengths, separately; said multiple order producing dispersive optics system further comprising one or more filter(s) which serve to pass wavelengths from only one produced order in regions in which adjacent produced orders spacially overlap, and to prevent stray light from having access to detector elements.

13. A multiple order producing dispersive optics system as in claim 12, in which at least one of said one or more filter(s) is of at least two section construction, with at least one section thereof being positioned in use so as to intercept wavelengths in a region of overlap between adjacent produced orders and allow wavelengths of essentially only one produced order to pass therethrough, and with another section thereof positioned so as to intercept and pass wavelengths of essentially only the same produced order and reject stray light which originates other than from said passed produced order.

14. A multiple order producing dispersive optics system as in claim 13, in which one section of at least one filter passes only wavelengths in the ultraviolet.

15. A multiple order producing optics system as in claim 12, in which the system selected from the group selected from a spectroscopic ellipsometer system and spectroscopic polarimeter system comprises:

a. a light source;

b. a polarization state generator;

c. a rotating analyzer;

d. a compensator;

e. a dispersive optics; and f. photodetector systems;

such that, during use, polychromatic light from said light source is caused to pass through said polarization state generator and is then caused to interact with a substrate system, thereby becoming typically elliptically polarized polychromatic light; such that said typically elliptically polarized polychromatic light is caused to pass through said rotating analyzer and become essentially linearly polarized, which essentially linearly polarized polychromatic light emerging from said rotating analyzer is then caused to pass through said compensator, such that said linearly polychromatic polarized light which exits said rotating analyzer is caused, by passage through said compensator, to become other than linearly polarized, which other than linearly polarized light which emerges from said compensator is then caused to interact with said dispersive optics and emerge therefrom as a plurality of produced orders, each of said produced orders comprising an essentially continuous spectrum of essentially single wavelengths which enter detector elements of intercepting photodetector systems for analysis therein.

16. A system selected from the group consisting of a spectroscopic ellipsometer and a spectroscopic polarimeter for use in sensing characteristics of a sample substrate system comprising:

a. a light source and polarization state generator;

b. an analyzer; and c. a dispersive optics positioned so as to receive a beam of polychromatic light which passes through the analyzer without refocusing after said beam of polychromatic light, which originates in said light source, interacts with said sample substrate system; wherein said dispersive optics produces multiple orders in use, each of said produced orders comprising an essentially continuous spectrum of spacially separated essentially single wavelength beams of light and being spacially separated from other present produced orders such that separate photodetector arrays intercept said separate produced orders, and wherein said dispersive optics directs incident polychromatic light onto produced order intercepting photodetector arrays at a predetermined angle with respect to a normal to said dispersive optics, with a precision of at least plus or minus one-half degree.

17. A system selected from the group consisting of a spectroscopic ellipsometer and a spectroscopic polarimeter for use in sensing characteristics of a sample substrate system as in claim 16, in which said dispersive optics is a diffraction grating.

18. A system selected from the group consisting of a spectroscopic ellipsometer and a spectroscopic polarimeter for use in sensing characteristics of a sample substrate system as in claim 16, in which said dispersive optics is a prism.

19. A system selected from the group consisting of a spectroscopic ellipsometer and a spectroscopic polarimeter for use in sensing characteristics of a sample substrate system as in claim 17, in which each of said multiple produced orders is spacially separated from other present produced orders such that separate photodetector arrays intercept separate produced orders and such that essentially single wavelength beams of light, which are spacially situated to close to one another in a single produced order for photo detector array detector elements in a single photo detector array to simultaneously access both separately, are simultaneously separately detectable in separate produced orders.

20. A system selected from the group consisting of a spectroscopic ellipsometer and a spectroscopic polarimeter for use in sensing characteristics of a sample substrate system as in claim 18, in which each of said multiple produced orders is spacially separated from other said produced orders such that separate photodetector arrays intercept separate produced orders and such that essentially single wavelength beams of light, which are spacially situated to close to one another in a single produced order for photo detector array detector elements in a single photo detector array to simultaneously access both separately, are simultaneously separately detectable in separate produced orders.

* * * * *